United States Patent [19]
Bell et al.

[11] Patent Number: 5,346,901
[45] Date of Patent: Sep. 13, 1994

[54] PYRAZOLOPYRIMIDINONE ANTIANGINAL AGENTS

[75] Inventors: Andrew S. Bell, Deal; David Brown, Nr Canterbury; Nicholas K. Terrett, Deal, all of United Kingdom

[73] Assignee: Pfizer Inc., New York, N.Y.

[21] Appl. No.: 84,827

[22] Filed: Jun. 29, 1993

Related U.S. Application Data

[60] Division of Ser. No. 882,988, May 14, 1992, Pat. No. 5,250,534, which is a continuation of Ser. No. 717,227, Jun. 14, 1991, abandoned.

Foreign Application Priority Data

Jun. 20, 1990 [GB]  United Kingdom .............. 9013750.6

[51] Int. Cl.$^5$ .................. A61K 31/505; C07D 487/04
[52] U.S. Cl. .................. 514/258; 514/236.2; 514/236.5; 544/118; 544/123; 544/262
[58] Field of Search .................. 514/236.2, 236.5, 258; 544/118, 123, 262

[56] References Cited

U.S. PATENT DOCUMENTS

| | | | |
|---|---|---|---|
| 4,052,390 | 10/1977 | Broughton et al. | 544/118 |
| 4,167,568 | 9/1979 | Knowles et al. | 544/254 |

FOREIGN PATENT DOCUMENTS

| | | | |
|---|---|---|---|
| 1095688 | 8/1988 | Australia | C07D 473/30 |
| 3309689 | 10/1989 | Australia | C07D 213/70 |
| 0201188 | 12/1986 | European Pat. Off. | C07D 487/04 |
| 0347146 | 12/1989 | European Pat. Off. | C07D 471/04 |
| 0349239 | 1/1990 | European Pat. Off. | C07D 487/04 |
| 0351058 | 1/1990 | European Pat. Off. | C07D 487/04 |
| 0352960 | 1/1990 | European Pat. Off. | C07D 473/30 |
| 0371731 | 6/1990 | European Pat. Off. | C07D 239/91 |

OTHER PUBLICATIONS

Hamilton et al., J. Med. Chem., 30 (1), 91–96, (1987).

Primary Examiner—Mukund J. Shah
Assistant Examiner—Y. N. Gupta
Attorney, Agent, or Firm—Peter C. Richardson; Gregg C. Benson; James T. Jones

[57] ABSTRACT

Compounds of the formula:

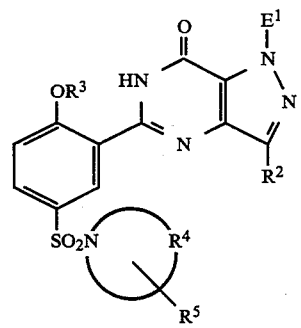

wherein $R^1$ is H, $C_1$–$C_3$ alkyl, $C_3$–$C_5$ cycloalkyl or $C_1$–$C_3$ perfluoroalkyl; $R^2$ is H, $C_1$–$C_6$ alkyl optionally substituted by OH, $C_1$–$C_3$ alkoxy or $C_3$–$C_6$ cycloalkyl, or $C_1$–$C_3$ perfluoroalkyl; $R^3$ is $C_1$–$C_6$ alkyl, $C_3$–$C_6$ alkynyl, $C_3$–$C_6$ alkynyl, $C_3$–$C_7$ cycloalkyl, $C_1$–$C_6$ perfluoroalkyl or ($C_3$–$C_6$ cycloalky)$C_1$–$C_6$ alkyl; $R^4$ taken together with the nitrogen atom to which it is attached completes a pyrrolidinyl, piperidino, morpholino, or 4-N-($R^6$)-piperazinyl group; $R^5$ is H, $C_1$–$C_4$ alkyl, $C_1$–$C_3$ alkoxy, $NR^7R^8$, or $CONR^7R^8$; $R^6$ is H, $C_1$–$C_6$ alkyl, ($C_1$–$C_3$ alkoxy) $C_2$–$C_6$ alkyl, hydroxy $C_2$–$C_6$ alkyl, ($R^7R^8$N)$C_2$–$C_6$ alkyl, ($R^7R^8$NCO)$C_1$–$C_6$ alkyl, $CONR^7R^8$, $CSNR^7R^8$ or $C(NH)NR^7R^8$; $R^7$ and $R^8$ are each independently H, $C_1$–$C_4$ alkyl, ($C_1$–$C_3$ alkoxy)$C_2$–$C_4$ alkyl or hydroxy $C_2$–$C_4$ alkyl; and pharmaceutically acceptable salts thereof, are selective cGMP PDE inhibitors useful in the treatment of cardiovascular disorders such as angina, hypertension, heart failure and atherosclerosis.

4 Claims, No Drawings

PYRAZOLOPYRIMIDINONE ANTIANGINAL AGENTS

This is a division of application Ser. No. 07/882,988, filed on May 14, 1992, now U.S. Pat. No. 5,250,534, which is a continuation of Ser. No. 07/717,227, filed on Jun. 14, 1991, abandoned.

Background of the Invention

This invention relates to a series of pyrazolo[4,3-d]-pyrimidin-7-ones, which are potent and selective inhibitors of cyclic guanosine 3′,5′-monophosphate phosphodiesterase (cGMP PDE), having utility in a variety of therapeutic areas including the treatment of various cardiovascular disorders such as angina, hypertension, heart failure and atherosclerosis.

The compounds of the invention exhibit selectivity for inhibition of cGMP PDEs rather than cyclic adenosine 3′,5′monophosphate phosphodiesterases (cAMP PDEs) and, as a consequence of this selective PDE inhibition, cGMP levels are elevated, which in turn can give rise to beneficial platelet anti-aggregatory, antivasospastic and vasodilatory activity, as well as potentiation of the effects of endothelium-derived relaxing factor (EDRF) and nitrovasodilators. Thus the compounds have utility in the treatment of a number of disorders, including stable, unstable and variant (Prinzmetal) angina, hypertension, congestive heart failure, atherosclerosis, conditions of reduced blood vessel patency e.g. post-percutaneous transluminal coronary angioplasty (post-PTCA), peripheral vascular disease, stroke, bronchitis, chronic asthma, allergic asthma, allergic rhinitis, glaucoma, and diseases characterised by disorders of gut motility, e.g. irritable bowel syndrome (IBS).

European patent application EP-A-0201188 discloses certain pyrazolo[4,3-d]pyrimidin-7-ones as adenosine receptor antagonists and PDE inhibitors, useful in the treatment of cardiovascular disorders such as heart failure or cardiac insufficiency. However these compounds are neither particularly potent PDE inhibitors, nor are they claimed to be selective inhibitors of cGMP PDE.

SUMMARY OF THE INVENTION

The compounds of the present invention are of the formula (I):

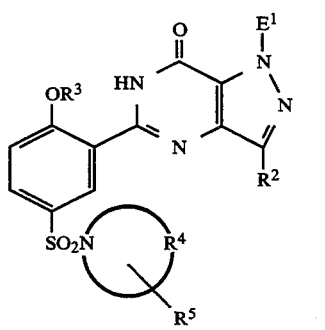

(I)

wherein $R^1$ is H, $C_1$-$C_3$ alkyl, $C_3$-$C_5$ cycloalkyl or $C_1$-$C_3$ perfluoroalkyl;

$R^2$ is H, $C_1$-$C_6$ alkyl optionally substituted by OH, $C_1$-$C_3$ alkoxy or $C_3$-$C_6$ cycloalkyl, or $C_1$-$C_3$ perfluoroalkyl;

$R^3$ is $C_1$-$C_6$ alkyl, $C_3$-$C_6$ alkenyl, $C_3$-$C_6$ alkynyl, $C_3$-$C_7$ cycloalkyl, $C_1$-$C_6$ perfluoroalkyl or ($C_3$-$C_6$ cycloalkyl)$C_1$-$C_6$ alkyl;

$R^4$ taken together with the nitrogen atom to which it is attached completes a pyrrolidinyl, piperidino, morpholino, or 4-N-($R^6$)-piperazinyl group;

$R^5$ is H, $C_1$-$C_4$ alkyl, $C_1$-$C_3$ alkoxy, $NR^7R^8$, or $CONR^7R^8$; $R^6$ is H, $C_1$-$C_6$ alkyl, ($C_1$-$C_3$ alkoxy)$C_2$-$C_6$ alkyl, hydroxy $C_2$-$C_6$ alkyl, ($R^7R^8N$)$C_2$-$C_6$ alkyl, ($R^7R^8NCO$)$C_1$-$C_6$ alkyl, $CONR^7R^8$, $CSNR^7R^8$ or $C(NH)NR^7R^8$;

$R^7$ and $R^8$ are each independently H, $C_1$-$C_4$ alkyl, ($C_1$-$C_3$ alkoxy)$C_2$-$C_4$ alkyl or hydroxy $C_2$-$C_4$ alkyl;

and pharmaceutically acceptable salts thereof.

In the above definition, unless otherwise indicated, alkyl or perfluoroalkyl groups having three or more carbon atoms may be straight or branched chain. In addition alkenyl or alkynyl groups having four or more carbon atoms, or alkoxy groups having three carbon atoms, may be straight or branched chain.

The compounds of formula (I) may contain one or more asymmetric centres and thus they can exist as enantiomers or diastereoisomers. The invention includes both mixtures and separate individual isomers.

The compounds of formula (I) may also exist in tautomeric forms and the invention includes both mixtures and separate individual tautomers.

Also included in the invention are radiolabelled derivatives of compounds of formula (I) which are suitable for biological studies.

The pharmaceutically acceptable salts of the compounds of formula (I) which contain a basic centre are acid addition salts formed with pharmaceutically acceptable acids. Examples include the hydrochloride, hydrobromide, sulphate or bisulphate, phosphate or hydrogen phosphate, acetate, citrate, fumarate, gluconate, lactate, maleate, succinate and tartrate salts. Compounds of the formula (I) can also provide pharmaceutically acceptable metal salts, particular alkali metal salts, with bases. Examples include the sodium and potassium salts.

A preferred group of compounds of the formula (I) is that wherein $R^1$ is H, methyl or ethyl; $R^2$ is $C_1$-$C_3$ alkyl optionally substituted by OH or methoxy; $R^3$ is $C_2$-$C_3$ alkyl or allyl; $R^4$ taken together with the nitrogen atom to which it is attached completes a piperidino or 4-N-($R^6$) piperazinyl group; $R^5$ is H, $NR^7R^8$ or $CONR^7R^8$; $R^6$ is H, $C_1$-$C_3$ alkyl, hydroxy $C_2$-$C_3$ alkyl, $CONR^7R^8$, $CSNR^7R^8$ or $C(NH)NR^7R^8$; and $R^7$ and $R^8$ are each independently H or methyl.

A particularly preferred group of compounds of the formula (I) is that wherein $R^1$ is methyl; $R^2$ is n-propyl; $R^3$ is ethyl, n-propyl or allyl; $R^4$ taken together with the nitrogen atom to which it is attached completes a 4-N-($R^6$) piperazinyl group; $R^5$ is H; and $R^6$ is H, $C_1$-$C_3$ alkyl or 2-hydroxyethyl.

Especially preferred individual compounds of the invention include:

5-[2-allyloxy-5-(4-methylpiperazinylsulphonyl)phenyl]-1-methyl-3-n-propyl-1,6-dihydro-7H-pyrazolo[4,3-d]pyrimdin-7-one;

5-[2-ethoxy-5-(piperazinylsulphonyl)phenyl]-1-methyl-3-n-propyl-1,6-dihydro-7H-pyrazolo[4,3-d]pyrimidin-7-one;

5-[2-ethoxy-5-(4-methylpiperazinylsulphonyl)phenyl]-1-methyl-3-n-propyl-1,6-dihydro-7H-pyrazolo[4,3-d]pyrimidin-7-one;

5-{2-ethoxy-5-[4-(2-propyl)piperazinylsulphonyl]-phenyl}-1-methyl-3-n-propyl-1,6-dihydro-7H-pyrazolo[4,3-d]pyrimidin-7-one;

5-{2-ethoxy-5-[4-(2-hydroxyethyl)piperazinylsulphonyl]-phenyl}-1-methyl-3-n-propyl-1,6-dihydro-7H-pyrazolo[4,3-d]-pyrimidin-7-one;

1-methyl-5-[5-piperazinylsulphonyl)-2-n-propoxyphenyl]-3-n-propyl-1,6-dihydro-7H-pyrazolo[4,3-d]pyrimidin-7-one; and 5-{5-[4-(2-hydroxyethyl)-piperazinylsulphonyl]-2-n-propoxyphenyl}-1-methyl-3-n-propyl-1,6-dihydro-7H-pyrazolo[4,3-d]-pyrimidin-7-one.

DETAILED DESCRIPTION OF THE INVENTION

The compounds of the general formula (I) may be prepared by the reaction of a compound of the general formula (II):

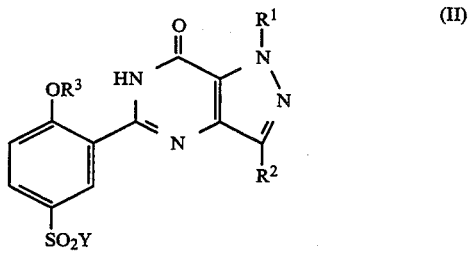

(wherein $R^1$, $R^2$ and $R^3$ are as previously defined, and Y represents a halogen atom, preferably a chlorine atom) with a compound of the general formula (III):

wherein $R^4$ and $R^5$ are as previously defined.

The reaction is generally carried out at room temperature, preferably in the presence of a solvent, for example an alkanol containing one to three carbon atoms, using an excess of (III) to scavenge the acid by-product (HY).

Compounds of the general formula (II) may be prepared from compounds of the general formula (IV):

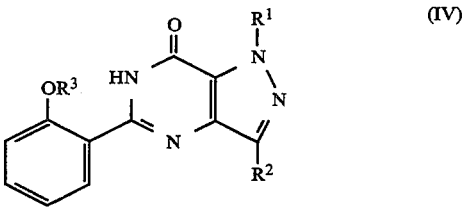

(wherein $R^1$, $R^2$ and $R^3$ are as previously defined) by the application of known methods for the introduction of a SO$_2$Y group (wherein Y is as previously defined) into an aromatic ring, for example, when Y represents a chlorine atom, by the action of chlorosulphonic acid at or near 0° C.

When $R^3$ is a group susceptible to removal under the chlorosulphonylation conditions, e.g. allyl, said group can be introduced in the final stage of the synthesis. Thus the phenol of the general formula (IV), wherein $R^3$ is H, and $R^1$ and $R^2$ are as previously defined, which is obtainable by Pd•-mediated deprotection of the O-allyl analogue as illustrated by Example 25, is chlorosulphonylated to provide a compound of the general formula (II), wherein Y is Cl, $R^3$ is H, and $R^1$ and $R^2$ are as previously defined. The latter is then reacted with the appropriate amine (III) to afford a compound of the general formula (I), wherein $R^3$ is H, and $R^1$, $R^2$, $R^4$ and $R^5$ are as previously defined, which is finally O-alkylated to furnish a compound of the general formula (I), wherein $R^1$, $R^2$, $R^3$, $R^4$ and $R^5$ are as defined for formula (I). The alkylation may be effected under standard conditions using the appropriate alkyl halide, e.g. allyl bromide, in the presence of a base such as potassium carbonate, in a suitable solvent, e.g. 2-butanone, at the reflux temperature of the reaction mixture. Alternatively, the alkylation may be achieved under conventional Mitsunobu reaction conditions.

In the case of other compounds of formula (IV) which may be incompatible with the chlorosulphonylation reaction conditions, e.g. those wherein $R^2$ is hydroxy $C_1$–$C_6$ alkyl, the hydroxy group can be protected with an acyl group such as acetyl or benzoyl. Said protecting group is subsequently removed at the final stage of the synthesis, under standard base hydrolysis conditions, to give compounds of the general formula (I) wherein $R^2$ is hydroxy $C_1$–$C_6$ alkyl, and $R^1$, $R^3$, $R^4$ and $R^5$ are as defined for formula (I). These latter compounds may also be obtained incidentally, as by-products, by chlorosulphonylation of the corresponding alkoxy analogues, i.e. compounds of the general formula (IV) wherein $R^2$ is ($C_1$–$C_3$ alkoxy)$C_1$–$C_6$ alkyl, followed by reaction of the crude product with the required amine (III), as illustrated by Example 48.

Compounds of the general formula (IV) may be prepared from compounds of the general formula (V):

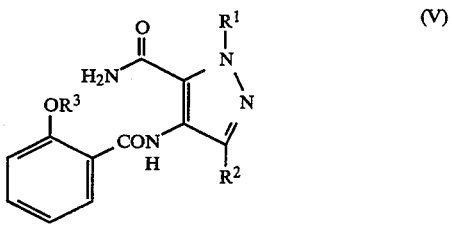

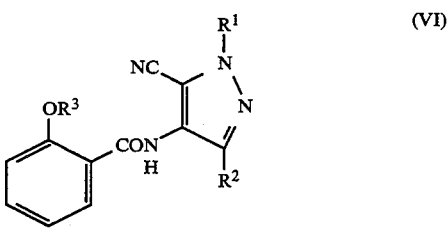

(wherein $R^1$, $R^2$ and $R^3$ are as previously defined) by the application of known cyclisation methods for pyrimidinone ring formation. Thus, for example, the cyclisation may be effected by the treatment of (V) with a base such as sodium hydroxide or potassium carbonate, optionally in the presence of hydrogen peroxide, in an ethanol-water medium at reflux temperature for 2–40 hours. Under these conditions the related nitrile of general formula (VI), wherein $R^1$, $R^2$ and $R^3$ are as previously defined, may also be employed as the precursor to (IV).

In an alternative cyclisation procedure, compounds of the general formula (IV) may be obtained by treatment of (V) with polyphosphoric acid at or near 140° C. for 6–18 hours.

Compounds of the general formulae (V) and (VI) may be prepared from compounds of the general formulae (VII) and (VIII) respectively:

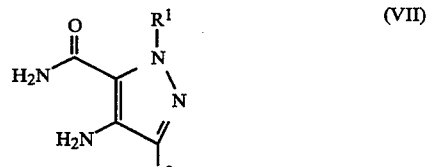
(VII)

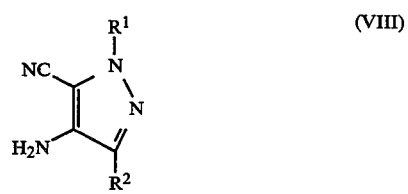
(VIII)

(wherein $R^1$ and $R^2$ are as previously defined) by reaction with a compound of general formula (IX):

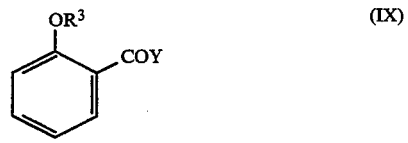
(IX)

(wherein $R^3$ and Y are as previously defined).

The reaction is generally carried out using an excess of (IX) in the presence of an excess of an aliphatic tertiary amine such as triethylamine to act as scavenger for the acid by-product (HY), optionally in the presence of a catalyst such as 4-dimethylaminopyridine, in an inert solvent such as dichloromethane at 0° C. to 25° C. for 2–6 hours.

The amines of formula (III), the aminopyrazoles of formulae (VII) and (VIII), and the acyl halides of formula (IX), when not commercially available, can be obtained by conventional synthetic procedures, in accordance with literature precedent, from readily accessible starting materials using standard reagents and reaction conditions.

Certain of the compounds of the general formula (I), wherein $R^4$ taken together with the nitrogen atom to which it is attached completes a 4-N-($R^6$)-piperazinyl group and $R^6$ is as previously defined but not hydrogen, may be prepared directly from the corresponding 4-N-unsubstituted piperazine analogue, that is a compound of the general formula (I) wherein $R^6$ is hydrogen, using appropriate standard synthetic procedures.

All of the above reactions are entirely conventional and appropriate reagents and conditions for their performance can readily be established by reference to standard text books and to the examples provided hereafter. Alternatives and variations will also be evident to the person skilled in the art to enable all the compounds defined by formula (I) to be prepared.

The biological activities of the compounds of the present invention were determined by the following test methods.

Phosphodiesterase activity

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson et al. (Biochem., 1971, 10, 311). The calcium/calmodulin (Ca/CAM)-independent cGMP PDE and the cGMP-inhibited cAMP PDE enzymes are obtained from rabbit platelets whilst, of the four major PDE enzymes of the rat kidney, the Ca/CAM-dependent cGMP PDE (fraction I) is isolated. Assays are performed using a modification of the "batch" method of W. J. Thompson and M. M. Appleman (Biochem., 1979, 18, 5228). Results from these tests show that the compounds of the present invention are potent and selective inhibitors of both cGMP PDEs.

Platelet anti-aggregatory activity

This is assessed by the determination of a compound's ability to inhibit platelet aggregation in vitro induced by platelet activating factor (PAF), and to potentiate the platelet antiaggregatory action in vitro of activators of guanylate cyclase such as nitroprusside and EDRF. Washed platelets are prepared essentially by the method of J. F. Mustard et al. (Methods in Enzymol., 1989, 169, 3) and aggregation is determined using standard turbidimetric techniques as described by G. V. R. Born, J. Physiol. (Lond), 1962, 162, 67P.

Antihypertensive activity

This is assessed following intravenous or oral administration of a compound to spontaneously hypertensive rats. Blood pressure is recorded via a cannula implanted in the carotid artery of either conscious or anaesthetised animals.

For administration to man in the curative or prophylactic treatment of angina, hypertension or congestive heart failure, oral dosages of the compounds will generally be in the range of from 4–800 mg daily for an average adult patient (70 kg). Thus for a typical adult patient, individual tablets or capsules contain from 2–400 mg of active compound, in a suitable pharmaceutically acceptable vehicle or carrier, for administration in single or multiple doses, once or several times per day. Dosages for intravenous, buccal or sublingual administration will typically be within the range of from 1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intravenously, intramuscularly, subcutaneously or intracoronarily. For parenteral administration, they are best used in the form of a sterile aqueous solution which may contain other substances, for example enough salts or glucose to make the solution isotonic with blood.

Thus in a further aspect the invention provides a pharmaceutical composition comprising a compound of the formula (I), or a pharmaceutically acceptable salt thereof, for use in medicine, particularly for the treatment of angina, hypertension or congestive heart failure, in a human being.

The invention further includes the use of a compound of the formula (I), or a pharmaceutically acceptable salt thereof, for the manufacture of a medicament for the treatment of stable, unstable and variant (Prinzmetal) angina, hypertension, congestive heart failure, athersclerosis, stroke, peripheral vascular disease, conditions of reduced blood vessel patency e.g. post-PTCA, chronic asthma, bronchitis, allergic asthma, allergic rhinitis, glaucoma, or diseases characterised by disorders of gut motility, e.g. IBS.

The preparation of the compounds of the invention will now be more particularly illustrated by reference to the following experimental Examples. The purity of the compounds was routinely monitored by thin layer chromatography (TLC) using Merck Kieselgel 60 $F_{254}$ plates. $^1$H-Nuclear magnetic resonance spectra were recorded using a Nicolet QE-300 spectrometer and were in all cases consistent with the proposed structures.

EXAMPLE 1

1-Methyl-3-n-propylpyrazole-5-carboxylic acid ethyl ester

A mixture of 3-n-propylpyrazole-5-carboxylic acid ethyl ester (24.1 g, 0.132 mol) (prepared by the method of Chem. Pharm. Bull., 1984, 32, 1568) and dimethyl sulphate (16.8 g, 0.133 mol) were heated to 90° C. for 2.5 hours. The mixture was dissolved in dichloromethane and the solution washed with sodium carbonate solution. The organic phase was separated, dried (MgSO$_4$) and evaporated under vacuum to give a solid. Chromatography on silica gel (300 g), eluting with dichloromethane gave the product as a colourless oil (20.4 g, 79%). Rf 0.8 (silica; dichloromethane, methanol, acetic acid; 80:20:1).

EXAMPLE 2

1-Methyl-3-n-propylpyrazole-5-carboxylic acid

1-Methyl-3-n-propylpyrazole-5-carboxylic acid ethyl ester (20.2 g, 0.10 mol) was suspended in 6N aqueous sodium hydroxide solution (50 ml, 0.30 mol). The mixture was heated to 80° C. for 2 hours then diluted with water (50 ml) and acidified with concentrated hydrochloric acid (25 ml). Filtration gave the carboxylic acid as pale brown crystals (12.3 g, 71%), m.p. 150°–154° C. Found: C, 56.99; H, 7.25; N,16.90. $C_8H_{12}N_2O_2$ requires C, 57.13; H, 7.19; N, 16.66%.

EXAMPLE 3

1-Methyl-4-nitro-3-n-propylpyrazole-5-carboxylic acid

1-Methyl-3-n-propylpyrazole-5-carboxylic acid (12.1 g, 0.072 mol) was added portionwise to a mixture of oleum (13 ml) and fuming nitric acid (11 ml), keeping the temperature below 60° C. After the addition, the mixture was heated at 60° C. overnight and then cooled to room temperature before being poured onto ice. Filtration of the precipitate gave the nitropyrazole as a white solid (11.5 g, 75%), m.p. 124°–127° C. Found: C, 45.43; H, 5.22; N, 19.42. $C_8H_{11}N_3O_4$ requires C, 45.57; H, 5.20; N, 19.71%.

EXAMPLE 4

1-Methyl-4-nitro-3-n-propylpyrazole-5-carboxamide

1-Methyl-4-nitro-3-n-propylpyrazole-5-carboxylic acid (11.3 g, 0.053 mol) was added to thionyl chloride (50 ml) and the resulting mixture heated under reflux for 3 hours. The reaction mixture was then cooled and excess thionyl chloride removed by evaporation under vacuum. The oily residue was dissolved in acetone (50 ml) and the solution cautiously added to a mixture of ice (50 g) and concentrated aqueous ammonium hydroxide solution (50 ml). The precipitate was collected by filtration to provide the pyrazolecarboxamide as a pale yellow solid (8.77 g, 78%), m.p. 141°–143° C. Found: C, 45.22; H, 5.71; N, 26.12. $C_8H_{12}N_4O_3$ requires C, 45.28; H, 5.70; N, 26.40%.

EXAMPLE 5

4-Amino-1-methyl-3-n-propylpyrazole-5-carboxamide

1-Methyl-4-nitro-3-n-propylpyrazole-5-carboxamide (3.45 g, 16.2 mmol) and stannous chloride dihydrate (18.4 g, 81 mmol) were suspended in ethanol and the mixture heated under reflux for 2 hours. The resulting solution was cooled to room temperature, basified to pH 9 by the addition of 2N aqueous sodium hydroxide solution and extracted with dichloromethane (3×150 ml). The organic extracts were combined, dried (MgSO$_4$) and evaporated under vacuum. Trituration of the residue with ether gave the aminopyrazole as an off-white solid (2.77 g, 94%), m.p. 98°–101° C. Found: C,52.84; H,7.81; N,30.38. $C_8H_{14}N_4O$ requires C,52.73; H,7.74; N,30.75%.

EXAMPLE 6

4-(2-Ethoxybenzamido)-1-methyl-3-n-propylpyrazole-5-carboxamide

A solution of 2-ethoxybenzoyl chloride (6.1 g, 33.0 mmol) in dichloromethane (50 ml) was added to a stirred solution of 4-amino-1-methyl-3-n-propylpyrazole-5-carboxamide (3.0 g, 16.4 mmol), 4-dimethylaminopyridine (0.02 g, 0.164 mmol) and triethylamine (3.34 g, 33.0 mmol) in dichloromethane (50 ml) at 0° C. The resulting mixture was allowed to warm to room temperature and stirred for a further 2 hours. The solvent was evaporated under vacuum, the residue dissolved in a 19:1 mixture of dichloromethane and methanol (250 ml), and then the solution washed with 1N hydrochloric acid (100 ml), dried (MgSO$_4$) and evaporated under vacuum. The crude material was chromatographed on silica gel (200 g), eluting with a 97:3 mixture of dichloromethane and methanol, to give a pink solid; crystallisation from ethyl acetate-hexane gave the pyrazole-5-carboxamide as a pale pink solid (2.2 g, 40%), m.p. 153°–155° C. Found: C,61.66; H,6.77; N,16.95. $C_{17}H_{22}N_4O_3$ requires C,61.80; H,6.71; N,16.96%.

EXAMPLE 7

5-(2-Ethoxyphenyl)-1-methyl-3-n-propyl-1,6-dihydro-7H-pyrazolo-[4,3-d]pyrimidin-7-one 4-(2-Ethoxybenzamido)-1-methyl-3-n-propyl-pyrazole-5-carboxamide (223 g, 0.676 mol) was added portionwise to a solution of sodium hydroxide (54 g, 1.35 mol) and 30% hydrogen peroxide solution (224 ml) in water (2000 ml). Ethanol (700 ml) was added and the resulting mixture heated under reflux for 2.5 hours, cooled, then evaporated under vacuum. The resulting solid was treated with 2N hydrochloric acid (380 ml), with external cooling, and the mixture was extracted with dichloromethane (1×700 ml, 3×200 ml). The combined organic extracts were washed successively with saturated aqueous sodium carbonate solution (3×400 ml) and brine (300 ml), then dried (Na$_2$SO$_4$) and evaporated under vacuum.

Chromatography of the residue on silica gel (1000 g), using a methanol in dichloromethane elution gradient (0–1%), followed by trituration of the crude product with ether (300 ml), gave the title compound as a colourless solid (152.2 g, 72%), m.p. 143°–146° C. Found: C,65.56; H,6.44; N,18.14. C$_{17}$H$_{20}$N$_4$O$_2$ requires C,65.36; H,6.45; N,17.94%.

EXAMPLE 8

5-(5-Chlorosulphonyl-2-ethoxyphenyl)-1-methyl-3-n-propyl-1,6-dihydro-7H-pyrazolo[4,3-d]pyrimidin-7-one 5-(2-Ethoxyphenyl)-1-methyl-3-n-propyl-1,6-dihydro-7H-pyrazolo[4,3-d]pyrimidin-7-one (10.0 g, 32.1 mmol) was added portionwise to chlorosulphonic acid (20 ml) at 0° C. under a nitrogen atmosphere. After being stirred overnight, the reaction solution was cautiously added to ice-water (150 ml) and the aqueous mixture extracted with a 9:1 mixture of dichloromethane and methanol (4×100 ml). The combined extracts were dried (Na$_2$SO$_4$) and evaporated under vacuum to give the required sulphonyl chloride as a white solid (12.8 g, 97%), m.p. 179°–181° C. Found: C,50.07; H,4.71; N,13.29. C$_{17}$H$_{19}$ClN$_4$O$_4$S requires C,49.70; H,4.66; N,13.64%.

EXAMPLE 9

5-[2-Ethoxy-5-(4-carbamoylpiperidinylsulphonyl)-phenyl]-1-methyl-3-n-propyl-1,6-dihydro-7H-pyrazolo[4,3-d]pyrimidin-7-one 4-Carbamoylpiperidine (703 mg, 5.50 mmol) was added to a stirred suspension of 5-(5-chlorosulphonyl-2-ethoxyphenyl)-1-methyl-3-n-propyl-1,6-dihydro-7H-pyrazolo[4,3-d]pyrimidin-7-one (750 mg, 1.80 mmol) in ethanol (50 ml) at room temperature. The resulting mixture was stirred for 4 days before removing the solvent by evaporation under vacuum. The residue was dissolved in a 9:1 mixture of dichloromethane and methanol (100 ml) and the solution washed with saturated aqueous sodium carbonate solution (100 ml). The aqueous phase was further extracted with dichloromethane-methanol mixtures (3×100 ml) and all the organic fractions were combined, dried (MgSO$_4$) and evaporated under vacuum to give a solid. Crystallisation from a mixture of methanol-dimethylformamide gave the title sulphonamide as an off-white solid (446 mg, 49%), m.p. 274°–276° C. Found: C,55.36; H,6.01; N,16.65. C$_{23}$H$_{29}$N$_6$O$_5$S requires C,55.08; H,5.83; N,16.75%.

EXAMPLES 10–14

The following compounds were prepared by the procedure of Example 9 using the appropriate amine.

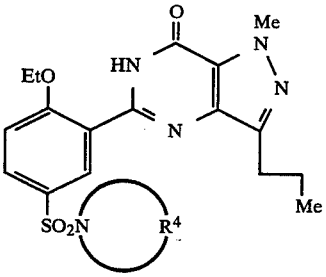

| Example | N R$^4$ | % yield | m.p. (°C.) | Analysis % (Theoretical in brackets) C | H | N |
|---|---|---|---|---|---|---|
| 10 | N⌒NH | 51 | 161–162 | 54.82 (54.77 | 6.13 6.13 | 17.95 18.25) |
| 11 | N⌒N–⟨OH | 79 | 194–196 | 54.63 (54.75 | 6.47 6.39 | 16.50 16.65) |
| 12 | N⌒NMe | 88 | 187–189 | 55.61 (55.68 | 6.23 6.37 | 17.74 17.71) |
| 13 | N⌒⟨–NMe$_2$ | 21 | 187–188 | 57.48 (57.35 | 6.74 6.82 | 16.47 16.72) |
| 14 | N⌒N$^i$Pr | 74 | 209–212 | 57.64 (57.35 | 6.66 6.82 | 16.81 16.72) |
| 15 | N⌒NCSNH$_2$ | 18 | 229–230 | 51.25 (50.85 | 5.56 5.63 | 18.92 18.87) |

EXAMPLE 16

5-{2-Ethoxy-5-[4-(methylthioimidoyl)piperazinylsulphonyl]phenyl}-1-methyl-3-n-propyl-1,6-dihydro-7H-pyrazolo[4,3-d]pyrimidin-7-one hydroiodide A mixture of 5-[2-ethoxy-5-(4-thiocarbamoylpiperazinylsulphonyl)phenyl]-1-methyl-3-n-propyl-1,6-dihydro-7H-pyrazolo[4,3-d]pyrimidin-7-one (0.78 g, 1.5 mmol), methyl iodide (426 mg, 3.0 mmol) and methanol (20 ml) was stirred under reflux for 2 hours, then allowed to cool. The resulting white solid was removed by filtration and crystallised from ethyl acetate-methanol to give the title compound as colourless crystals (0.70 g, 71%), m.p. 227°–228° C. Found: C,41.43; H,4.79; N,14.42. C$_{23}$H$_{31}$N$_7$O$_4$S$_2$; HI requires C,41.75; H,4.88; N,14.82%.

EXAMPLE 17

5-{2-Ethoxy-5-[4-(methylamidino)piperazinylsulphonyl]phenyl}-1-methyl-3-n-propyl-1,6-dihydro-7H-pyrazolo[4,3-d]pyrimidin-7-one hydroiodide 5-{2-Ethoxy-5-[4-methylthioimidoyl)piperazinylsulphonyl]phenyl}-1-methyl-3-n-propyl-1,6-dihydro-7H-pyrazolo[4,3-d]-pyrimidin-7-one hydroiodide (0.5 g, 0.75 mmol) was added to a 33% solution of methylamine in ethanol (20 ml) and the mixture stirred at room temperature for 18 hours. The solution was evaporated under vacuum and the residue triturated with ether. Chromatography of the resulting solid on silica gel (10 g), using a methanol in dichloromethane elution gradient (0–4%), followed by trituration of the crude product with ether, gave a light brown powder. Crystallisation from ethyl acetate-methanol gave the title compound as colourless crystals (112 mg, 23%), m.p. 253°–255° C. Found: C,42.90; H,5.09; N,17.41. $C_{23}H_{32}N_8O_4S$; HI requires C,42.86; H,5.16; N,17.39%.

EXAMPLE 18

1-Methyl-4-(2-n-propoxybenzamido)-3-n-propyl-pyrazole-5-carboxamide

This amide was prepared from 2-n-propoxybenzoyl chloride following the procedure described in Example 6 and was obtained as a pink solid (63%), m.p. 148°–149° C. Found: C,62.97; H,7.00; N,16.29. $C_{18}H_{24}N_4O_3$ requires C,62.77; H,7.02; N,16.27%.

EXAMPLE 19

1-Methyl-5-(2-n-propoxyphenyl)-3-n-propyl-1,6-dihydro-7H-pyrazolo[4,3-d]pyrimidin-7-one 1-Methyl-4-(2-n-propoxybenzamido)-3-n-propyl-pyrazole-5-carboxamide (0.34 g, 0.99 mmol) was added to a stirred mixture of 30% hydrogen peroxide solution (1.0 ml), potassium carbonate (0.54 g, 3.92 mmol), water (10 ml) and ethanol (5 ml). The mixture was heated under reflux for 38 hours and then evaporated under vacuum. The residue was suspended in water (20 ml), then the mixture acidified with 2N hydrochloric acid and extracted with dichloromethane (3×20 ml). The extracts were combined, dried (Na₂SO₄) and evaporated under vacuum. The resulting residue was chromatographed on silica gel (6 g), using a methanol in dichloromethane elution gradient (0.0–1.0%), to give an oil, successive trituration of which with ether gave the required product as a white solid (0.19 g, 59%), m.p. 111°–114° C. Found: C,66.26; H,6.92; N,17.15. $C_{18}H_{22}N_4O_2$ requires C,66.23; H,6.80; N,17.17%.

EXAMPLE 20

5-(5-Chlorosulphonyl-2-n-propoxyphenyl)-1-methyl-3-n-propyl-1,6-dihydro-7H-pyrazolo[4,3-d]pyrimidin-7-one This sulphonyl chloride was prepared from 5-(2-n-propoxyphenyl-1-methyl-3-n-propyl-1,6-dihydro-7H-pyrazolo[4,3-d]pyrimidin-7-one following the procedure of Example 8 and was obtained as a white solid (92%). Found: C,51.26; H,5.02; N,12.90. $C_{18}H_{21}ClN_4O_4S$ requires C,50.88; H,4.98; N,13.19%.

EXAMPLE 21

1-Methyl-5-[5-(piperazinylsulphonyl)-2-n-propoxyphenyl]-3-n-propyl-1,6-dihydro-7H-pyrazolo[4,3-d]pyrimidin-7-one This sulphonamide was prepared from piperazine and 5-(5-chlorosulphonyl-2-n-propoxyphenyl)-1-methyl-3-n-propyl-1,6-dihydro-7H-pyrazolo[4,3-d]pyrimidin-7-one following the procedure of Example 9 and was obtained as a white solid (70%), m.p. 185°–186° C. Found: C,56.17; H,6.38; N,17.65. $C_{22}H_{30}N_6O_4S$ requires C,55.67; H,6.37; N,17.71%.

EXAMPLE 22

5-{5-[4-(2-Hydroxyethyl)piperazinylsulphonyl]-2-n-propoxyphenyl}-1-methyl-3-n-propyl-1,6-dihydro-7H-pyrazolo[4,3-d]pyrimidin-7-one This sulphonamide was prepared from N-(2-hydroxyethyl)-piperazine and 5-(5-chlorosulphonyl-2-n-propoxyphenyl)-1-methyl-3-n-propyl-1,6-dihydro-7H-pyrazolo[4,3-d]pyrimidin-7-one following the procedure of Example 9 and was obtained as colourless needles (66%), m.p. 158°–159° C. Found: C,55.83; H,6.58; N,16.13. $C_{24}H_{34}N_6O_5S$ requires C,55.58; H,6.61; N,16.20%.

EXAMPLE 23

4-(2-Allyloxybenzamido)-1-methyl-3-n-propylpyrazole-5-carboxamide

A solution of 2-allyloxybenzoyl chloride (3.93 g, 0.02 mol) in dichloromethane (20 ml) was added dropwise to a stirred, partial solution of 4-amino-1-methyl-3-n-propylpyrazole-5-carboxamide (3.64 g, 0.02 mol) in pyridine (50 ml), and the resulting mixture stirred at room temperature overnight in a dry atmosphere. The solvent was evaporated under vacuum and the residue partitioned between dichloromethane (50 ml) and saturated aqueous sodium carbonate solution (50 ml). The organic layer was separated and the aqueous layer exhaustively extracted with further dichloromethane. The combined organic solutions were washed with 2M HCl (3×30 ml), then brine (1×30 ml), and dried (Na₂SO₄). After filtration and evaporation under vacuum of the filtrate, the crude product was crystallised from ethyl acetate to give the title compound (4.525 g, 66%), m.p. 132°–134° C. Found: C,63.49; H,6.42; N,16.33. $C_{18}H_{22}N_4O_3$ requires C,63.14; H,6.48; N,16.36%.

EXAMPLE 24

5-(2-Allyloxyphenyl)-1-methyl-3-n-propyl-1,6-dihydro-7H-pyrazolo[4,3-d]pyrimidin-7-one A mixture of 4-(2-allyloxybenzamido)-1-methyl-3-n-propyl-pyrazole-5-carboxamide (1.2 g, 0.0035 mol), sodium hydroxide (0.70 g, 0.018 mol), water (34 ml) and ethanol (8 ml) was refluxed for 5 hours. After cooling, the solution was exhaustively extracted with ethyl acetate. The combined extracts were washed with brine (30 ml), dried (Na₂SO₄), filtered and the solvent evaporated under vacuum to give a crude product which was crystallised from ethyl acetate/hexane to afford the title compound (0.476 g, 37%), m.p. 116°–119° C. Found: C,67.00; H,6.21; N,17.23. $C_{18}H_{20}N_4O_2$ requires C,66.65; H,6.21; N,17.27%.

EXAMPLE 25

5-(2-Hydroxyphenyl)-1-methyl-3-n-propyl-1,6-dihydro-7H-pyrazolo[4,3-d]pyrimidin-7-one A mixture of 5-(2-allyloxyphenyl)-1-methyl-3-n-propyl-1,6-dihydro-7H-pyrazolo[4,3-d[pyrimidin-7-one (0.25 g, 0.0008 mol), phenol (0.145 g, 0.0015 mol), piperidine (0.131 g, 0.0015 mol) and tetrakis(triphenylphosphine)palladium(0) (0.046 g, 0.00004 mol) in absolute ethanol (5 ml) was refluxed overnight under nitrogen. The mixture was allowed to cool, the solvent evaporated under vacuum and the residue dissolved in ethyl acetate (40 ml). This solution was washed with water (3×10 ml), 1M HCl (3×10 ml) and brine (1×10 ml). After drying (Na$_2$SO$_4$) and filtration, the filtrate was evaporated under vacuum to give the crude product. The title phenol (0.021 g, 10%) was obtained after trituration with diethyl ether and crystallisation from ethyl acetate/pentane, m.p. 233°–238° C. Found: C,63.17; H,5.65; N,19.52. C$_{15}$H$_{16}$N$_4$O$_2$ requires C,63.36; H,5.67; N,19.71%.

EXAMPLE 26

5-(5-Chlorosulphonyl-2-hydroxyphenyl)-1-methyl-3-n-propyl-1,6-dihydro-7H-pyrazolo[4,3-d]pyrimidin-7-one 5-(2-Hydroxyphenyl)-1-methyl-3-n-propyl-1,6-dihydro-7H-pyrazolo[4,3-d]pyrimidin-7-one (0.239 g, 0.00084 mol) was added, in portions, to stirred chlorosulphonic acid (3 ml) cooled to 0° C. under a nitrogen atmosphere, and the resulting deep red solution stirred at room temperature for 18 hours. The reaction mixture was then added dropwise, with care, to stirred ice/water to give a brown solid. The latter mixture was extracted with dichloromethane (3×30 ml), the combined extracts dried (Na$_2$SO$_4$) and filtered, and the filtrate evaporated under vacuum to give a brown solid (0.24 g, 75%), used in the next step without further purification; Rf 0.3 (silica; dichloromethane, methanol; 95:5).

EXAMPLE 27

5-[2-Hydroxy-5-(4-methylpiperazinylsulphonyl)-phenyl]-1-methyl-3-n-propyl-1,6-dihydro-7H-pyrazolo[4,3-d]pyrimidin-7-one A solution of 5-(5-chlorosulphonyl-2-hydroxyphenyl)-1-methyl-3-n-propyl-1,6-dihydro-7H-pyrazolo[4,3-d]pyrimidin-7-one (0.235 g, 0.0006 mol) and N-methylpiperazine (0.5 ml, 0.0045 mol) in ethanol (40 ml) was stirred at room temperature for 18 hours. The solution was evaporated under vacuum and the residue partitioned between ethyl acetate (40 ml) and water (40 ml). The fine precipitate was filtered off, washed with water then ethyl acetate, and crystallised from ethyl acetate/DMF to give the title compound as an off-white powder (0.260 g, 49%), m.p. 283°–284° C. Found: C,53.53; H,5.89; N,18.40. C$_{20}$H$_{26}$N$_6$O$_4$S requires C,53.80; H,5.87; N,18.82%.

EXAMPLE 28

5-[2-Allyloxy-5-(4-methylpiperazinylsulphonyl)-phenyl]-1-methyl-3-n-propyl-1,6-dihydro-7H-pyrazolo[4,3-d]pyrimidin-7-one Allyl bromide (0.02 ml, 0.00023 mol) was added to a stirred suspension of 5-[2-hydroxy-5-(4-methylpiperazinylsulphonyl)-phenyl]-1-methyl-3-n-propyl-1,6-dihydro-7H-pyrazolo[4,3-d]-pyrimidin-7-one (0.103 g, 0.00023 mol) and potassium carbonate (0.032 g, 0.00023 mol) in 2-butanone (10 ml) and the mixture heated under reflux for 8 hours. After cooling, the reaction mixture was evaporated under vacuum and the residue suspended in water (20 ml). The aqueous suspension was extracted with ethyl acetate (3×20 ml), the combined extracts dried (Na$_2$SO$_4$) and, after filtration, evaporated under vacuum to give an oil. Column chromatography on silica gel (2 g) using a methanol in. dichloromethane elution gradient (0–3%), followed by evaporation under vacuum of appropriate fractions, gave a semi-solid which was dissolved in acetone; evaporation under vacuum of the solution gave the title compound (0.011 g, 10%), m.p. 151°–153° C., Rf 0.5 (silica; dichloromethane, methanol; 95:5), m/e 487 (M$^+$ +1).

EXAMPLE 29

4-(2-Ethoxybenzamido)-1,3-dimethylpyrazole-5-carboxamide

This amide was prepared from 4-amino-1,3-dimethylpyrazole-5-carboxamide (prepared by the method of J. Med. Chem 1987, 30, 91), following the procedure of Example 6, and was obtained as a white solid (81%), m.p. 178°–181° C. Found: C,59.89; H,6.05; N,18.44. C$_{15}$H$_{18}$N$_4$O$_3$ requires C,59.59; H,6.00; N,18.53%.

EXAMPLE 30

5-(2-Ethoxyphenyl)-1,3-dimethyl-1,6-dihydro-7H-pyrazolo[4,3-d]-pyrimidin-7-one 4-(2-Ethoxybenzamido)-1,3-dimethylpyrazole-5-carboxamide (1.6 g, 5.29 mmol) was added to polyphosphoric acid (50 g) and the mixture heated to 140° C. for 6 hours. The solution was cooled, poured into ice-water (100 ml), and then the mixture was basified with 10% aqueous sodium hydroxide solution and extracted with dichloromethane (3×100 ml). The organic extracts were combined, dried (MgSO$_4$) and evaporated under vacuum. The residue was chromatographed on silica gel eluting with a 97:3 mixture of dichloromethane and methanol. Crystallisation of the crude product from aqueous ethanol gave the title compound as a colourless solid, m.p. 201°–204° C. Found: C,63.43; H,5.57; N,19.35. C$_{15}$H$_{16}$N$_4$O$_2$ requires C,63.36; H,5.67; N,19.71%.

EXAMPLE 31

5-(5-Chlorosulphonyl-2-ethoxyphenyl)-1,3-dimethyl-1,6-dihydro-7H-pyrazolo[4,3-d]pyrimidin-7-one This sulphonyl chloride was prepared from 5-(2-ethoxyphenyl)-1,3-dimethyl-1,6-dihydro-7H-pyrazolo[4,3-d]pyrimidin-7-one, following the procedure of Example 8, and was obtained in quantitative yield as a white solid. Rf 0.3 (silica:ether). It was used without further purification.

EXAMPLES 32–34

The following compounds were prepared from 5-(5-chlorosulphonyl-2-ethoxyphenyl)-1,3-dimethyl-1,6-dihydro-7H-pyrazolo[4,3-d]pyrimidin-7-one and the appropriate amine following the procedure of Example 9.

[Structure diagram showing a compound with EtO, HN, SO2N-R4, and a pyrazole ring with Me groups]

| Example | N‿R⁴ | % yield | m.p. (°C.) | Analysis % (Theoretical in brackets) C | H | N |
|---|---|---|---|---|---|---|
| 32 | N‿NMe | 68 | 225–226 | 53.88 (53.79 | 5.81 5.87 | 18.42 18.82) |
| 33 | N‿NH | 68 | 240–242 | 53.07 (52.76 | 5.77 5.59 | 19.27 19.43) |
| 34 | N‿N⌒OH | 62 | 228–229 | 53.23 (52.93 | 5.87 5.92 | 17.72 17.63) |

EXAMPLE 35

4-Nitro-3-n-propylpyrazole-5-carboxylic acid 3-n-Propylpyrazole-5-carboxylic acid (prepared by the method of Chem. Pharm. Bull. 1984, 32, 1568), was nitrated following the procedure of Example 3, to give the title compound as a colourless solid (75%), m.p. 169°–173° C. Found: C,42.35; H,4.56; N,21.07. $C_7H_9N_3O_4$ requires C,42.21; H,4.55; N,21.10%.

EXAMPLE 36

4-Nitro-3-n-propylpyrazole-5-carboxamide

A mixture of 4-nitro-3-n-propylpyrazole-5-carboxylic acid (7.8 g, 39.2 mmol) and thionyl chloride (35 ml) was heated under reflux for 3 hours. The solvent was removed by evaporation under vacuum and the solid residue was added portionwise to aqueous ammonium hydroxide solution (40 ml) at 0° C. The mixture was then diluted with water (60 ml) and extracted with a 9:1 mixture of dichloromethane and methanol (3×100 ml). The organic fractions were combined, dried (MgSO₄) and evaporated under vacuum, and the residue crystallised from ethanol to give the carboxamide as a colourless solid (1.0 g, 13%), m.p. 202°–206° C. Found: C,42.35; H,5.01; N,28.38. $C_7H_{10}N_4O_3$ requires C,42.42; H,5.09; N,28.27%.

EXAMPLE 37

4-Amino-3-n-propylpyrazole-5-carboxamide

A solution of 4-nitro-3-n-propylpyrazole-5-carboxamide (198 mg, 1.0 mmol) in methanol (5 ml) was added dropwise to a mixture of sodium borohydride (113 mg, 2.97 mmol), 10% palladium on carbon (5 mg) and water (3 ml). The mixture was stirred at room temperature for 3 hours, filtered and the solvent removed by evaporation under vacuum. Crystallisation of the residue from ethyl acetate-methanol gave the title compound as an off-white solid (61 mg, 36%), m.p. 196°–201° C. Rf 0.4 (silica; dichloromethane, methanol, ammonium hydroxide; 90:10:1). Found: C,48.96; H,6.98; N,32.08. $C_7H_{12}N_4O$ requires C,49.98; H,7.19; N,33.31%.

EXAMPLE 38

4-(2-Ethoxybenzamido)-3-n-propylpyrazole-5-carboxamide

The title amide was prepared from 4-amino-3-n-propylpyrazole-5-carboxamide following the procedure of Example 6, and was obtained as a white solid (64%), m.p. 209°–211° C. Found: C,60.73; H,6.41; N,17.80. $C_{16}H_{20}N_4O_3$ requires C,60.74; H,6.37; N,17.71%.

EXAMPLE 39

5-(2-Ethoxyphenyl)-3-n-propyl-1,6-dihydro-7H-pyrazolo[4,3-d]-pyrimidin-7-one The title compound was prepared from 4-(2-ethoxybenzamido)-3-n-propyl-pyrazole-5-carboxamide following the procedure of Example 30 and was obtained as a white solid (16%), m.p. 199°–201° C. Found: C,64.44; H,6.19; N,18.44%. $C_{16}H_{18}N_4O_2$ requires C,64.41; H,6.08; N,18.78%.

EXAMPLE 40

5-(5-Chlorosulphonyl-2-ethoxyphenyl)-3-n-propyl-1,6-dihydro-7H-pyrazolo[4,3-d]pyrimidin-7-one The title sulphonyl chloride was prepared from 5-(2-ethoxyphenyl)-3-n-propyl-1,6-dihydro-7H-pyrazolo[4,3-d]-pyrimidin-7-one following the procedure of Example 8 and was obtained as a white solid (78%). Rf 0.25 (silica;ether).

It was used without further purification.

EXAMPLE 41

5-[2-Ethoxy-5-(4-methylpiperazinyl)sulphonylphenyl]-3-n-propyl-1,-6-dihydro-7H-pyrazolo[4,3-d]pyrimidin-7-one The title sulphonamide was prepared from 5-(5-chlorosulphonyl-2-ethoxyphenyl)-3-n-propyl-1,6-dihydro-7H-pyrazolo[4,3-d]pyrimidin-7-one following the procedure of Example 9 and was obtained as a white solid (70%), m.p. 236°–239° C. Found: C,54.84; H,6.27; N,18.10. $C_{21}H_{28}N_6O_4S$ requires C,54.76; H,6.13; N,18.25%.

EXAMPLE 42

3-Bromomethyl-5-chloro-1-methyl-4-nitropyrazole

N-Bromosuccinimide (10.7 g, 60.0 mmol) was added to a solution of 5-chloro-1,3-dimethyl-4-nitropyrazole (8.78 g, 50.0 mmol) in carbon tetrachloride (100 ml) and the solution was heated under reflux whilst being irradiated with visible light (150 W tungsten lamp) for 3 days. At intervals throughout the reaction, quantities of benzoyl peroxide (6×50 mg) were added. The solvent was removed by evaporation under vacuum and the residue chromatographed on silica gel eluting with a 1:1 mixture of dichloromethane and hexane to give the bromide as an off-white solid (8.0 g, 63%), m.p. 80°–82° C. Found: C,23.95; H,2.05; N,16.31. $C_5H_5BrClN_3O_2$ requires C,23.60; H,1.98; N,16.51%.

EXAMPLE 43

5-Chloro-3-methoxymethyl-1-methyl-4-nitropyrazole

A solution of 3-bromomethyl-5-chloro-1-methyl-4-nitropyrazole (5.0 g, 19.6 mmol) in methanol (50 ml) was treated with silver nitrate (5.75 g, 33.8 mmol) and the mixture heated under reflux for 2 hours. The cooled reaction mixture was filtered and the filtrate evaporated under vacuum. The residue was partitioned between ethyl acetate (100 ml) and water (50 ml) and the aqueous phase extracted with a further quantity of ethyl acetate (50 ml). The organic extracts were combined, dried (MgSO$_4$) and evaporated under vacuum. Chromatography on silica gel, eluting with a 97:3 mixture of dichloromethane and methanol, gave the title pyrazole as a white solid (1.6 g, 40%), m.p. 59°–63° C. Found: C,34.65; H,3.83; N,20.05. C$_6$H$_8$ClN$_3$O$_3$ requires C,35.05; H,3.92; N,20.44%.

EXAMPLE 44

5-Cyano-3-methoxymethyl-1-methyl-4-nitropyrazole

A solution of 5-chloro-3-methoxymethyl-1-methyl-4-nitropyrazole (205 mg, 1.0 mmol), potassium cyanide (130 mg, 2.0 mmol) and 18-crown-6 (10 mg) in acetonitrile (2 ml) was heated under reflux overnight. The solvent was evaporated under vacuum and the residue partitioned between ethyl acetate (20 ml) and water (20 ml). The organic phase was separated, dried (MgSO$_4$) and evaporated under vacuum, then the residue chromatographed on silica gel eluting with a 1:1 mixture of ethyl acetate and pentane. Trituration of the crude product with ether provided a yellow solid (38 mg, 19%), m.p. 48°–50° C. Found: C,42.89; H,4.15; N,28.78. C$_7$H$_8$N$_4$O$_3$ requires C,42.86; H,4.11; N,28.56%.

EXAMPLE 45

4-Amino-5-cyano-3-methoxymethyl-1-methylpyrazole

The title compound was prepared from 5-cyano-3-methoxymethyl-1-methyl-4-nitropyrazole following the procedure of Example 5 and was obtained as an off-white solid (68%), m.p. 82°–84° C. Found: C,50.81; H,6.13; N,33.94. C$_7$H$_{10}$N$_4$O requires C,50.59; H,6.07; N,33.72%

EXAMPLE 46

5-Cyano-4-(2-ethoxybenzamido)-3-methoxymethyl-1-methylpyrazole

The title compound was prepared from 4-amino-5-cyano-3-methoxymethyl-1-methylpyrazole following the procedure of Example 6 and was obtained as an off-white solid (61%), m.p. 103°–105° C. Found: C,61.21; H,5.98; N,17.80. C$_{16}$H$_{18}$N$_4$O$_3$ requires C,61.13; H,5.77; N,17.83%.

EXAMPLE 47

5-(2-Ethoxyphenyl)-3-methoxymethyl-1-methyl-1,6-dihydro-7H-pyrazolo[4,3-d]pyrimidin-7-one The title compound was prepared from 5-cyano-4-(2-ethoxybenzamido)-3-methoxymethyl-1-methylpyrazole following the procedure of Example 7, via in situ generation of the 5-primary amide derivative, and was obtained as a white solid (38%), m.p. 160°–161° C. Found: C,61.35; H,5.75; N,17.98. C$_{16}$H$_{18}$N$_4$O$_3$ requires C,61.13; H,5.77; N,17.83%.

EXAMPLE 48

3-Methoxymethyl-1-methyl-5-[5-(4-methylpiperazinylsulphonyl)-2-ethoxyphenyl]1,6-dihydro-7H-pyrazolo[4,3-d]pyrimidin-7-one 5-(2-Ethoxyphenyl)-3-methoxymethyl-1-methyl-1,6-dihydro-7H-pyrazolo[4,3-d]pyrimidin-7-one (470 mg, 1.50 mmol) was dissolved in chlorosulphonic acid (3 ml) at 0° C. The solution was stirred at room temperature for 2 hours, then cautiously added to ice-water (50 ml). The resulting solution was neutralised with saturated sodium carbonate solution, then extracted with a 20:1 mixture of dichloromethane and methanol (2×50 ml). The combined organic extracts were evaporated under vacuum and the residue was dissolved in ethanol (5 ml) and the solution treated with N-methylpiperazine (450 mg, 4.5 mmol). After 1 hour at room temperature the solvent was evaporated under vacuum and the residue chromatographed on silica gel, eluting with a mixture of dichloromethane, methanol and aqueous ammonium hydroxide solution (90:10:1 by volume). Trituration of the crude product with ethyl acetate gave the title compound as a white solid (49 mg, 7%), m.p. 198°–199° C. Found: C,52.94; H,6.04; N,17.67. C$_{21}$H$_{28}$N$_6$O$_5$S requires C,52.93; H,5.92; N,17.64%.

Also isolated following chromatography and crystallisation from a mixture of ethyl acetate and methanol was 3-hydroxymethyl-1-methyl-5-[5-(4-methylpiperazinylsulphonyl)-2-ethoxyphenyl]-1,6-dihydro-7H-pyrazolo[4,3-d]pyrimidin-7-one as a white solid (51 mg, 7%), m.p. 209°–210° C. Found: C,51.94; H,5.77; N,18.05. C$_{20}$H$_{26}$N$_6$O$_5$S requires C,51.94; H,5.67; N,18.17%.

EXAMPLE 49

1-Ethyl-3-n-propylpyrazole-5-carboxylic acid ethyl ester

This pyrazole was prepared from 3-n-propylpyrazole-5-carboxylic acid ethyl ester and diethyl sulphate, following the procedure described in Example 1, and was obtained as a colourless oil (72%). Rf 0.5 (silica; ethyl acetate, hexane; 1:1).

EXAMPLE 50

1-Ethyl-3-n-propylpyrazole-5-carboxylic acid

This carboxylic acid was prepared from 1-ethyl-3-n-propylpyrazole-5-carboxylic acid ethyl ester, following the procedure described in Example 2, and was obtained as a pale brown solid (89%), m.p. 73°–77° C. Found C, 58.62; H,7.69 ; N,15.23. C$_9$H$_{14}$N$_2$O$_2$ requires C,59.32; H,7.74; N,15.37%.

EXAMPLE 51

1-Ethyl-4-nitro-3-n-propylpyrazole-5-carboxylic acid

The title compound was prepared from 1-ethyl-3-n-propylpyrazole-5-carboxylic acid, following the procedure described in Example 3, and was obtained as a colourless solid (96%), m.p. 120°–123° C. Found: C,47.61; H,5.81; N,18.54. C$_9$H$_{13}$N$_3$O$_4$ requires C,47.57; H,5.77; N,18.49%.

EXAMPLE 52

1-Ethyl-4-nitro-3-n-propylpyrazole-5-carboxamide

The title amide was prepared from 1-ethyl-4-nitro-3-n-propylpyrazole-5-carboxylic acid, following the procedure described in Example 4, and was obtained as an off-white solid (86%), m.p. 119°–120° C. Found: C,47.38; H,6.18; N,24.34. $C_9H_{14}N_4O_3$ requires C,47.78; H,6.24; N,24.77%

EXAMPLE 53

4-Amino-1-ethyl-3-n-propylpyrazole-5-carboxamide

The title compound was prepared from 1-ethyl-4-nitro-3-n-propylpyrazole-5-carboxamide, by the procedure described in Example 5, and was obtained as an off-white solid (100%), m.p. 93°–97° C. Found: C,55.17; H,8.34; N,28.93. $C_9H_{16}N_4O$ requires C,55.08; H,8.22; N,28.55%.

EXAMPLE 54

4-(2-Ethoxybenzamido)-1-ethyl-3-n-propylpyrazole-5-carboxamide

The title amide was prepared from 4-amino-1-ethyl-3-n-propylpyrazole-5-carboxamide and 2-ethoxybenzoyl chloride, following the procedure described in Example 6, and was obtained as a colourless solid (73%), m.p. 139°–141° C. Found: C,63.03; H,7.15; N,16.50. $C_{18}H_{24}N_4O_3$ requires C,62.77; H,7.02; N,16.27%.

EXAMPLE 55

5-(2-Ethoxyphenyl)-1-ethyl-3-n-propyl-1,6-dihydro-7H-pyrazolo[4,3-d]pyrimidin-7-one The title compound was prepared from 4-(2-ethoxybenzamido)-1-ethyl-3-n-propylpyrazolo-5-carboxamide following the procedure of Example 7, and was obtained as a colourless solid (46%), m.p. 112°–114° C. Found: C,66.59; H,6.85; N,17.26. $C_{18}H_{22}N_4O_2$ requires C,66.23; H,6.79; N,17.17%.

EXAMPLE 56

5-(5-Chlorosulphonyl-2-ethoxyphenyl)-1-ethyl-3-n-propyl-1,6-dihydro-7H-pyrazolo[4,3-d]pyrimidin-7-one The title compound was prepared from 5-(2-ethoxyphenyl)-1-ethyl-3-n-propyl-1,6-dihydro-7H-pyrazolo[4,3-d]pyrimidin-7-one following the procedure of Example 8, and was obtained as a methylene chloride solvate (86%), m.p. 170°–172° C. Found: C,49.82; H,4.84; N,12.77. $C_{18}H_{21}ClN_4O_4S$; $1/6CH_2Cl_2$ requires C,49.70; H,4.90; N,12.77%.

EXAMPLE 57

5-[2-Ethoxy-5-(4-methylpiperazinylsulphonyl)phenyl]-1-ethyl-3-n-propyl-1,6-dihydro-7H-pyrazolo[4,3-d]pyrimidin-7-one The title sulphonamide was prepared from 5-(5-chlorosulphonyl-2ethoxyphenyl)-1-ethyl-3-n-propyl-1,6-dihydro-7H-pyrazolo[4,3-d]pyrimidin-7-one and N-methylpiperazine following the procedure of Example 9 and was obtained as a colourless solid (43%), m.p. 160°–162° C. Found: C,57.24; H,6.17; N,16.83. $C_{23}H_{32}N_6O_4S$ requires C,56.54; H,6.60; N,17.20%. Rf 0.35 (silica; dichloromethane, methanol; 9:1).

EXAMPLE 58

5-{2-Ethoxy-5-[4-(2-hydroxyethyl)piperazinylsulphonyl]phenyl}-1-ethyl-3-n-propyl-1,6-dihydro-7H-pyrazolo[4,3-d]pyrimidin-7-one The title sulphonamide was prepared from 5-(5-chlorosulphonyl-2-ethoxyphenyl)-1-ethyl-3-n-propyl-1,6-dihydro-7H-pyrazolo[4,3-d]pyrimidin-7-one and N-(2-hydroxyethyl)piperazine following the procedure of Example 9 and was obtained as a colourless solid (88%), m.p. 191°–193° C. Found: C,55.74; H,6.55; N,15.78. $C_{24}H_{34}N_6O_5S$ requires C,55.58; H,6.61; H,16.20%.

We claim:

1. A compound of the formula:

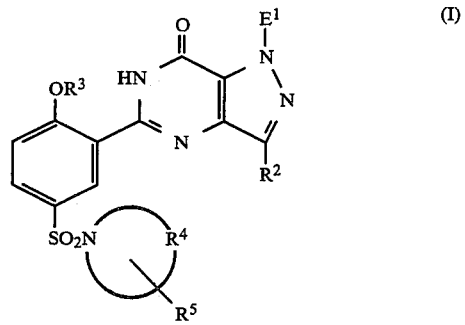

wherein
- $R^1$ is H, $C_1$–$C_3$ alkyl, $C_3$–$C_5$ cycloalkyl or $C_1$–$C_3$ perfluoroalkyl;
- $R^2$ is H, $C_1$–$C_6$ alkyl optionally substituted by OH, $C_1$–$C_3$ alkoxy or $C_3$–$C_6$ cycloalkyl, or $C_1$–$C_3$ perfluoroalkyl;
- $R^3$ is $C_1$–$C_6$ alkyl, $C_3$–$C_6$ alkenyl, $C_3$–$C_6$ alkynyl, $C_3$–$C_7$ cycloalkyl, $C_1$–$C_6$ perfluoroalkyl or ($C_3$–$C_6$ cycloalkyl)$C_1$–$C_6$ alkyl;
- $R^4$ taken together with the nitrogen atom to which it is attached completes a pyrrolidinyl, piperidino, or morpholino group;
- $R^5$ is H, $C_1$–$C_4$ alkyl, $C_1$–$C_3$ alkoxy, $NR^7R^8$, or $CONR^7R^8$;
- $R^7$ and $R^8$ are each independently H, $C_1$–$C_4$ alkyl, ($C_1$–$C_3$ alkoxy)$C_2$–$C_4$ alkyl or hydroxy $C_2$–$C_4$ alkyl; and pharmaceutically acceptable salts thereof.

2. A compound as claimed in claim 1 wherein $R^1$ is H, methyl or ethyl; $R^2$ is $C_1$–$C_3$ alkyl optionally substituted by OH or methoxy; $R^3$ is $C_2$–$C_3$ alkyl or allyl; $R^4$ taken together with the nitrogen atom to which it is attached completes a piperidino group; $R^5$ is H, $NR^7R^8$ or $CONR^7R^8$; and $R^7$ and $R^8$ are each independently H or methyl.

3. A pharmaceutical composition comprising a compound of the formula (I) or a pharmaceutically acceptable salt thereof, as claimed in any one of claims 1 to 2, together with a pharmaceutically acceptable diluent or carrier.

4. A method of treating, in a human being, angina, hypertension, heart failure or atherosclerosis which comprises administering to said human being an effective amount of a compound of the formula (I) or a pharmaceutically acceptable salt thereof, as claimed in any one of claims 1 to 2, or a pharmaceutical composition as claimed in claim 3.

* * * * *